United States Patent
Amith et al.

(10) Patent No.: US 10,130,620 B2
(45) Date of Patent: Nov. 20, 2018

(54) LIQUID PHARMACEUTICAL COMPOSITION FOR ORAL ADMINISTRATION COMPRISING FEXOFENADINE

(71) Applicant: AVENTISUB LLC, Greenville, DE (US)

(72) Inventors: Kumar Amith, Gurdaspur (IN); Prajapati Dilip, Gujarat (IN); Prasad Kum, Hyderabad (IN); Khullar Praveen, Dona Paula (IN); Kumar Ramesh, Sheohar (IN)

(73) Assignee: AVENTISUB LLC, Greenville, DE (US)

( * ) Notice: Subject to any disclaimer, the term of this patent is extended or adjusted under 35 U.S.C. 154(b) by 0 days.

(21) Appl. No.: 14/392,229

(22) PCT Filed: Jul. 1, 2014

(86) PCT No.: PCT/IB2014/062754
§ 371 (c)(1),
(2) Date: Dec. 23, 2015

(87) PCT Pub. No.: WO2015/001478
PCT Pub. Date: Jan. 8, 2015

(65) Prior Publication Data
US 2016/0184284 A1    Jun. 30, 2016

(30) Foreign Application Priority Data
Jul. 1, 2013   (IN) .......................... 2919/CHE/2013

(51) Int. Cl.
*A61K 31/445* (2006.01)
*A61K 9/00* (2006.01)
*A61K 9/08* (2006.01)
*A61K 47/10* (2017.01)
*A61K 47/26* (2006.01)

(52) U.S. Cl.
CPC .......... *A61K 31/445* (2013.01); *A61K 9/0053* (2013.01); *A61K 9/0095* (2013.01); *A61K 9/08* (2013.01); *A61K 47/10* (2013.01); *A61K 47/26* (2013.01)

(58) Field of Classification Search
CPC ...... A61K 31/445; A61K 47/10; A61K 47/26; A61K 9/0053; A61K 9/0095; A61K 9/08
See application file for complete search history.

(56) References Cited

U.S. PATENT DOCUMENTS

| | | |
|---|---|---|
| 5,049,568 A | 9/1991 | Kristof et al. |
| 6,113,942 A | 9/2000 | Ortyl et al. |
| 8,933,097 B2 | 1/2015 | Chrzan et al. |
| 2008/0274196 A1 | 11/2008 | Jayanthi et al. |

FOREIGN PATENT DOCUMENTS

| | | |
|---|---|---|
| JP | 2009-503058 A | 1/2009 |
| WO | WO-2007/017905 A1 | 2/2007 |

OTHER PUBLICATIONS

International Search Report and Written Opinion for PCT Application No. PCT/IB2014/062754 filed on Jul. 1, 2014; eight pages.
Strides Arcolab Limited. (Apr. 5, 2006). "Liquid Oral Formulation Containing Antihistamine," Specification of Indian Patent Application No. 538/MUM/2006, seven pages.

*Primary Examiner* — Sarah Pihonak
(74) *Attorney, Agent, or Firm* — Morrison & Foerster LLP

(57) ABSTRACT

The present invention relates to a liquid pharmaceutical composition for oral administration comprising fexofenadine and/or a pharmaceutically acceptable salt thereof, a pharmaceutically acceptable carrier which is either polyethylene glycol or a propylene glycol-based solvent, or a mixture thereof, from 35 to 90% wt. of a pharmaceutical excipient stabilizing fexofenadine and/or a pharmaceutically acceptable salt thereof, said pharmaceutical excipient consisting of glycerol with optionally sorbitol. The invention also relates to the uses of these compositions as a medicament and to the process for preparing said compositions.

10 Claims, No Drawings

LIQUID PHARMACEUTICAL COMPOSITION FOR ORAL ADMINISTRATION COMPRISING FEXOFENADINE

CROSS REFERENCE TO RELATED APPLICATIONS

This application is a National Phase application under 35 U.S.C. § 371 of International Application No. PCT/IB2014/062754 filed Jul. 1, 2014, which claims priority benefit to IN Application No. 2919/CHE/2013 filed Jul. 1, 2013, the disclosures of which are herein incorporated by reference in their entirety.

The present invention relates to a liquid pharmaceutical composition of fexofenadine and/or a pharmaceutically acceptable salt thereof for oral administration, wherein the composition is a clear stable solution.

The present invention also concerns a process for preparing the oral liquid pharmaceutical composition and the use of said pharmaceutical composition as a medicament.

Fexofenadine [(+)-4-[1-hydroxy-4-[4(hydroxydiphenyl-methyl)-1-piperidinyl-butyl]-α, α-dimethyl benzene acetic acid] is a well-known antihistamine compound with a selective peripheral HI-receptor antagonist activity. Fexofenadine as a substance is usually used in the form of fexofenadine hydrochloride represented by formula (I) below:

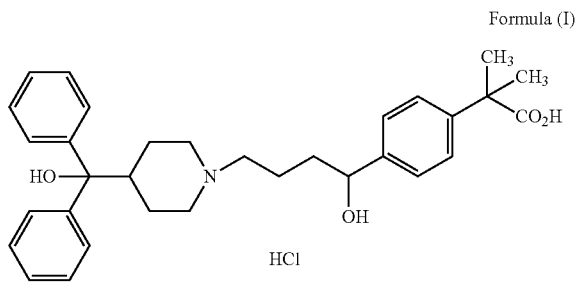 [SMILES: CC(C)(C(=O)O)c1ccc(C(O)CCCN2CCC(C(O)(c3ccccc3)c3ccccc3)CC2)cc1 ; Cl]

Formula (I)

The process for preparing fexofenadine hydrochloride is known from U.S. Pat. No. 6,113,942. Moreover, fexofenadine hydrochloride is commercially available under the name ALLEGRA®.

Fexofenadine has poor solubility in aqueous solutions, and its formulation presents difficult problems for effective administration to patients. A well-designed formulation should, at a minimum, be capable of presenting a therapeutically effective amount of the hydrophobic compound to the desired absorption site, in an absorbable form. Even this minimal functionality is difficult to achieve when the delivery of the hydrophobic therapeutic agent requires interaction with aqueous physiological environments, such as gastric fluids and intestinal fluids. Furthermore, drug absorption in different individuals might differ significantly due to differences in gastrointestinal function and food intake. Therefore, it is rather difficult to determine and control the dosage.

Fexofenadine is unique in that it appears to be non-sedating, even at higher doses in in vitro models. Efflux transporter P-glycoprotein (P-gp) has been reported to transport fexofenadine and it is considered to be an important determinant of fexofenadine pharmacokinetics. Since fexofenadine is the substrate of P-gp and several organic anion transporting polypeptides (OATP), food and co-administration of drugs have significant effect on its oral bioavailability. Furthermore, another challenge in the formulation of fexofenadine in oral administrable forms is its low solubility, especially in gastric conditions (solubility of 0.2 mg of fexofenadine HCl per ml of pH 1.2 aqueous buffer solution).

Yet another difficulty in the formulation of fexofenadine in oral pharmaceutical compositions is its unpleasant, strong and bitter taste and after-taste which has led to poor or even non-compliance with the treatment and, thus, has a negative impact on the efficiency of the treatment.

Also, fexofenadine hydrochloride has reduced oral bioavailability (up to 33%) because of first pass metabolism due to involvement of P-Glycoprotein metabolic pathway.

Allegra® brand fexofenadine is conventionally available as Allegra 30 mg and 60 mg twice-daily Tablets; Allegra 180 mg once-daily Tablet and as well as a liquid suspension for oral administration for children such as Allegra Paediatric Suspension. This antihistamine is specially formulated for children, because it is raspberry-flavoured, does not cause drowsiness, has a rapid onset of action and an anti-inflammatory effect. It is indicated for children aged 2 to 11 years and for the treatment of symptoms associated with urticaria in children aged 6 months to 11 years.

The Allegra® Paediatric Suspension, which is known from US patent application US2008/0274196, contains preservatives and sugars that limit the applicability or desirability of this oral liquid dosage form of the drug. This formulation includes parabens, such as butyl-paraben, methyl-paraben and propyl-paraben. Parabens, however, have been linked to negative health effect, including drug allergies. Butyl paraben has been determined to have effects on human reproduction, with negative effects on spermatogenesis. The paraben has been included to ensure that the liquid dosage forms maintain the stability of the composition.

Allegra® also includes natural sugars such as sucrose, which is a disaccharide composed of the monosaccharide glucose and fructose with the molecular formula $C_{12}H_{22}O_{11}$. Sugars have typically been included, in addition to being a sweetener, to enhance the flavour of fexofenadine liquid composition and to mask or minimize the bitter or unpleasant taste associated with fexofenadine. However, there has been increasing consumer demand for healthier pharmaceutical formulations and compositions. Moreover, many consumers prefer avoiding caloric intake when consuming drugs and these consumers are particularly keen to use formulations that avoid unnecessary calories while retaining a palatable flavour. For example, sugar-free formulations are desirable for diabetics, pregnant women, and paediatric population, populations that typically are required or requested to limit sugar consumption.

It is now desired to obtain a clear stable liquid dosage form of fexofenadine and/or a pharmaceutically acceptable salt thereof, such as fexofenadine hydrochloride, that avoids the problems of the prior art.

The present invention provides an orally administrable, stable liquid pharmaceutical composition, comprising fexofenadine and/or a pharmaceutically acceptable salt thereof. The composition has improved chemical and physical stability, suitability for children, while maintaining bioavailability and having good microbiological properties. These properties can be obtained due to in particular the interaction between the drug and the accompanied ingredients, selection of optimal mixing ratio of the respective ingredients and use of specific water content.

By "chemical stability", it is meant a liquid composition which, in particular, exhibits high resistance against decomposition of fexofenadine, or a pharmaceutically acceptable salt thereof, in particular, fexofenadine hydrochloride. Thus, upon storage for 1, 2, 3 or 6 months at 40° C. and 75% humidity, the pharmaceutical composition according to the present invention usually does not exhibit high levels of decomposition (with a total impurity level of less than 3% wt., preferably less than 2% wt. by weight of the fexofenadine or its pharmaceutically acceptable salt) and contains at least 97% wt., preferably at least 98% wt. and most preferably at least 99% wt. by weight of the initial content of fexofenadine or its pharmaceutically acceptable salt (as evidenced by HPLC analysis).

By "physical stability", it is meant a liquid composition which keeps a clear appearance (transparency) upon storage. In particular, upon storage for 1, 2, 3 or 6 months at 40° C. and 75% humidity, pharmaceutical composition according to the present invention usually does not exhibit any cloudiness.

The present invention can advantageously meet one or more of the unmet needs of the art by providing the inventive compositions and methods.

The present invention provides a liquid pharmaceutical composition for oral administration comprising:
 a pharmaceutically effective amount of fexofenadine and/or a pharmaceutically acceptable salt thereof,
 a pharmaceutically acceptable carrier which is either polyethylene glycol or a propylene glycol-based solvent, or a mixture thereof,
 from 35 to 90% wt. of a pharmaceutical excipient stabilizing fexofenadine and/or a pharmaceutically acceptable salt thereof, said pharmaceutical excipient consisting of glycerol optionally with sorbitol,
the weight percentage being relative to the total weight of the composition.

It should be noted that throughout the present application, ranges are intended to include the limits.

Fexofenadine introduced into the composition preferably is a salt of fexofenadine, more preferably, fexofenadine hydrochloride, as represented by formula (I) above. Fexofenadine hydrochloride exists under three forms, depending on the degree of hydration of the salt. Preferably, fexofenadine hydrochloride is in form I, i.e. anhydrous.

In the composition of the present invention, the fexofenadine hydrochloride is present in amounts ranging from 0.05% wt. to 2% wt. by weight of the composition. In a preferred embodiment, the fexofenadine hydrochloride is present in an amount ranging from 0.1% wt. to 1% wt. by weight of the composition. For example, fexofenadine hydrochloride is present at about 0.5% wt. by weight of the composition.

Alternatively, the fexofenadine hydrochloride is present in amounts ranging from 20 mg/5 mL to 40 mg/5 mL of the composition. In a preferred embodiment the fexofenadine hydrochloride is present in an amount ranging from 25 mg/5 mL to 35 mg/5 mL of the composition. For example, fexofenadine hydrochloride is present in an amount ranging from 30 mg/5 mL of the composition.

The exact dose of active agent and the particular formulation to be administered depend on a number of factors, e.g., the condition to be treated, the desired duration of the treatment and the release rate of the active agent. For instance, the required amount of the fexofenadine hydrochloride and the release rate thereof may be determined on the basis of known in vitro or in vivo techniques, determining how long a particular active agent concentration in the blood plasma remains at an acceptable level for a therapeutic effect.

Fexofenadine and its pharmaceutically acceptable salts are known to be difficult to solubilize and stabilize.

This solubilisation and stabilization can be achieved by the use of a specific combination of a pharmaceutically acceptable carrier and a pharmaceutical excipient stabilizing fexofenadine or/and its pharmaceutically acceptable salt. In particular, the composition according to the invention comprises no β-cyclodextrin.

At least one pharmaceutically acceptable carrier, present in the composition according to the invention, is either polyethylene glycol (PEG) or a propylene glycol-based solvent, or a mixture thereof.

By "propylene glycol-based solvent", it is meant propylene glycol or a phospholipid concentrate comprising propylene glycol. An example of a phospholipid concentrate comprising propylene is sold under the trade name Phosal 50 PG.

Examples of PEG useful in the present invention include, but are not limited to, PEG 200, PEG 300, PEG 400, PEG 600 or mixtures thereof. In some embodiments, the PEG is PEG 400.

In the composition of the present invention, the pharmaceutically acceptable carrier which is either polyethylene glycol or a propylene glycol-based solvent, or a mixture thereof, is present in amounts ranging from 1 to 6% wt., preferably 2 to 5% wt. and more preferably, 2.5 to 4.5% wt. by weight of the composition. For example, this pharmaceutically acceptable carrier is present at about 2% wt. by weight of the composition Alternatively, the total amount of this pharmaceutically acceptable carrier is from 50 to 250 mg/5 mL of the composition. For example, this pharmaceutically acceptable carrier is present at about 175 mg/5 mL of the composition.

In a preferred embodiment, this pharmaceutically acceptable carrier is a mixture of polyethylene glycol and propylene glycol (PG). In that embodiment, the total amount of PEG is advantageously from 0.05 to 2% wt., preferably 0.2 to 1.5% wt., more preferably 0.5 to 1% wt. by weight of the composition, and the total amount of PG is advantageously from 1.3 to 3.5% wt., preferably, 1.5 to 2.5% wt. by weight of the composition.

Propylene glycol and/or polyethylene glycol act as solubilizing and stabilizing agents in combination with the pharmaceutical excipient stabilizing fexofenadine or its pharmaceutical salt, and help in enhancing bioavailability of fexofenadine, in particular when the water content is very low (6% wt. by weight of the composition or less). Propylene glycol is also a known antimicrobial.

Advantageously, the weight ratio of fexofenadine hydrochloride to the pharmaceutically acceptable carrier which is either a polyethylene glycol or a propylene glycol-based solvent, or a mixture thereof, is from 1:1 to 1:15. In a preferred embodiment of the invention, the weight ratio of fexofenadine hydrochloride to said pharmaceutically acceptable carrier is from 1:5 to 1:13 and most preferably this ratio is equal to 1:8 or 1:10.

An additional pharmaceutically acceptable carrier can be present in the composition. In that case, by "additional pharmaceutically acceptable carrier", it is meant a carrier, such as a solvent, suspending agent or vehicle, for delivering the compound or compounds in question. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

Preferably, the total amount of the pharmaceutical excipient stabilizing fexofenadine or its pharmaceutically salt, is advantageously from 50 to 90% wt., preferably from 60 to 90% wt., more preferably from 75 to 90% wt. by weight of the composition.

In a first embodiment, the pharmaceutical excipient is glycerol.

Glycerol (or glycerin) is present in amounts ranging from 50% wt. to 90% wt., preferably 70% wt. to 90% wt. by weight of the composition. For example, glycerol is present at about 85% wt. by weight of the composition.

Alternatively, glycerol is present in amounts ranging from 2350 mg/5 mL to 6000 mg/5 mL, preferably 4000 mg/5 mL to 5500 mg/5 mL of the composition. For example, fexofenadine hydrochloride is present at about 5000 mg/5 mL of the composition.

In a second embodiment, the pharmaceutical excipient is a combination of glycerol with sorbitol.

In that embodiment, glycerol is present in amounts ranging from 25% wt. to 50% wt., preferably 30% wt. to 45% wt. by weight of the composition. For example, glycerol is present at about 38% wt. by weight of the composition.

Alternatively, glycerol is present in amounts ranging from 1500 mg/5 mL to 4000 mg/5 mL, preferably 2000 mg/5 mL to 3000 mg/5 mL of the composition. For example, glycerol is present at about 2350 mg/5 mL of the composition.

In that embodiment, sorbitol is present in amounts ranging from 20% wt. to 50% wt., preferably 25% wt. to 40% wt. by weight of the composition. For example, sorbitol is present at about 33.5% wt. by weight of the composition.

Alternatively, sorbitol is introduced under a sorbitol solution at 70% wt. of sorbitol by weight of solution and is present in amounts ranging from 1600 mg/5 mL to 4000 mg/5 mL, preferably 2000 mg/5 mL to 3500 mg/5 mL of the composition. For example, sorbitol solution at 70% w/w is present at about 2970 mg/5 mL of the composition.

In that case, sorbitol solution at 70% wt. of sorbitol is present in amounts ranging from 28% wt. to 72% wt., preferably 35% wt. to 58% wt. by weight of the composition. For example, sorbitol is present at about 48% wt. by weight of the composition.

In general, higher amounts of sorbitol may reduce the stability of the composition.

Additionally, the presence of glycerol and sorbitol advantageously avoids the use of sucrose in the compositions, sucrose being caloric and cariogenic.

It should be noted that the liquid pharmaceutical composition according to the invention is a clear solution.

The liquid pharmaceutical composition according to the invention further comprises at least one sugar substitute, at least one chelating agent and/or at least one flavouring agent. Preferably, the composition comprises at least one sugar substitute, at least one chelating agent and at least one flavouring agent By sugar substitute, it is meant a food additive that replicates the taste of sugar. Preferably, said sugar substitute is at least a high intensity sweetener with optionally one or more polyol. Preferably, the high intensity sweetener is sucralose, saccharine and its salts, and the polyol is xylitol, mannitol, glycerol, sorbitol, hydrogenated starch hydrolysates and/or maltitol.

Advantageously, the total content of sugar substitute(s) is within a range from 4% wt. to 12% wt. by weight of the composition.

One particular advantage of the composition according to the invention is that it is substantially or entirely free of saccharide sugars.

As used herein, "substantially free" is understood to be less than 3% wt. by weight, preferably less than 2% wt. by weight, and more preferably less than 1% wt. by weight, of the undesired component. In a preferred embodiment, the term "substantially free" refers to less than 0.5% wt. by weight, preferably less than 0.15% wt. by weight, and more preferably less than 0.05 or 0.01% wt. by weight of the composition.

As used herein, "entirely free" is understood to mean an absence, i.e., less than an analytically detectable amount, of the stated excipients.

In a preferred embodiment, the composition is entirely free of all saccharide sugars. As used herein, "saccharide sugar" means sugar consisting of monosaccharides and/or disaccharides, which are commonly referred to as sugars. Examples of monosaccharides include glucose (dextrose), fructose (levulose), galactose, xylose and ribose. Monosaccharides are the building blocks of disaccharides such as sucrose.

The compositions according to the invention surprisingly and unexpectedly provide a taste-masking effect despite being at least substantially free, more preferably entirely free, of saccharide sugars in the formulation. It was also surprisingly and unexpectedly observed that the composition according to the invention maintains the bioavailability of fexofenadine despite being at least substantially free, more preferably entirely free, of saccharide sugars in the formulation and despite the fact that saccharide sugars have an influence on the bioavailability of fexofenadine.

By chelating agent, it is meant an agent to prevent oxidation due to metal ions. Any suitable chelating agent can be introduced in the composition. Preferably, the chelating agent is a pharmaceutically salt of ethylenediaminetetraacetic acid (EDTA), such as di-sodium EDTA.

Advantageously, the total content of the chelating agent(s) is within a range from 0.05% wt. to 0.15% wt. by weight of the composition.

The flavouring agent is preferably a sugar-free flavouring agent available to those of ordinary skill in the art. Examples of suitable flavouring agents include one or more of menthol, peppermint, anise, and any fruit flavour, such as one or more grapefruit, orange, lime, lemon, strawberry, cherry, raspberry. Such flavouring agent(s), if present, may be at a content of 0.1% wt. to 0.5% wt. by weight of the composition.

Excipients, other than the pharmaceutical excipient stabilizing fexofenadine or its pharmaceutically acceptable salt, can be included in the composition, in an amount and as a type that do not substantially detrimentally affect stability or lack of sugar in the composition. Such excipients may include, but are not limited to, diluents, taste-masking components and colouring agents.

Preferably, the pH of the composition is comprised within the range of 3 to 6, more preferably, 3.5 to 5.5. The best results have been achieved for a pH comprised between 4 and 5. These selected ranges of a pH guarantee an appropriate storage stability of the composition and improve its storage stability and its shelf-life.

In the composition of the present invention, the water content is sufficiently low in order to limit the development and the growth of microorganisms. Advantageously, the water content of the composition is below 30%, preferably, below 25% and more preferably below 20% wt. by weight of the composition.

Preferably, extra water added into the composition is at minimum and is purified water according to the U.S. and E.U. pharmacopeias. By "extra water", it is meant water which is not introduced in the composition via the formulation of another ingredient. For example, some ingredients, such as sorbitol, may include water in their formulation.

In a preferred embodiment, the composition according to the invention comprises less than 9% wt. of extra water, preferably less than 6% wt. and more preferably less than 5% wt. by weight of the composition.

More particularly, in an embodiment of the composition comprising glycerol and a sorbitol solution at 70%, the extra water content should be less than 6% wt. and more preferably less than 5% wt. by weight of the composition.

This extra water content is advantageous allowing the total water content of the composition to be as low as possible. Consequently, the composition can be substantially or entirely free of preservatives, in particular, substantially or entirely free of parabens.

In a preferred embodiment, the composition is entirely free of all parabens. In one embodiment, the microbiological stability of the composition according to the invention is greater than the conventional fexofenadine liquid formulation, particularly the Allegra® Paediatric Suspension that contains parabens. In another embodiment, the liquid composition degrades at most about 20% more rapidly than conventional paraben-containing formulation, more preferably at most 10% more rapidly, and most preferably is substantially equivalent in stability.

The composition according to the invention provides an antimicrobial effect (i.e. refers to the inhibition, management, or delayed growth of bacteria or other microbes in the formulation over the time) despite being at least substantially free, more preferably entirely free, of all parabens in the formulation.

In a first preferred specific embodiment, the composition according to the invention comprises only glycerol as pharmaceutical excipient stabilizing fexofenadine hydrochloride and comprises the following ingredients:
- 0.05% wt. to 2% wt., preferably 0.1% wt. to 1% wt., more preferably about 0.5% wt. of fexofenadine hydrochloride by weight of the composition
- 0.05% to 2% wt., preferably 0.2% to 1.5% wt., more preferably 0.5% to 1% wt. of polyethylene glycol,
- 1.3% to 3.5% wt., preferably, 1.5% to 2.5% wt. of propylene glycol,
- 50% wt. to 90% wt., preferably 70% wt. to 90% wt., more preferably about 85% wt. of glycerol,
- 0.1% wt. to 0.5% wt. of flavouring agent(s),
- 4% wt. to 12% wt. of a sugar substitute, preferably sucralose and xylitol,
- 0.05% wt. to 0.15% wt. of a chelating agent, preferably disodium EDTA, and
- less than 9% wt., preferably less than 6% wt. and more preferably less than 5% wt. of extra water the weight percentage being relative to the total weight of the composition and pH being of about 4.0 to 5.0.

In a second preferred specific embodiment, the composition according to the invention comprises a combination of glycerol and sorbitol as pharmaceutical excipient stabilizing fexofenadine hydrochloride and comprises the following ingredients:
- 0.05% wt. to 2% wt., preferably 0.1% wt. to 1% wt., more preferably about 0.5% wt. of fexofenadine hydrochloride by weight of the composition
- 0.05% to 2% wt., preferably 0.2% to 1.5% wt., more preferably 0.5% to 1% wt. of polyethylene glycol,
- 1.3% to 3.5% wt., preferably, 1.5% to 2.5% wt. of propylene glycol,
- 25% wt. to 50% wt., preferably 30% wt. to 45% wt. and more preferably about 38% wt. of glycerol,
- 20% wt. to 50% wt., preferably 25% wt. to 40% wt. and more preferably about 33.5% wt. of sorbitol,
- 0.1% wt. to 0.5% wt. of flavouring agent(s),
- 4% wt. to 12% wt. of a sugar substitute, preferably sucralose and xylitol,
- 0.05% wt. to 0.15% wt. of a chelating agent, preferably disodium EDTA, and
- less than 9% wt., preferably less than 6% wt. and more preferably less than 5% wt. of extra water the weight percentage being relative to the total weight of the composition and pH being of about 4.0 to 5.0.

The pharmaceutical composition according to the invention can be used as a medicament, in particular as an antihistamine and/or a bronchodilator, and is particularly suitable for the treatment of allergies and/or urticaria, preferably in humans, especially in infants or children. Furthermore, the pharmaceutical composition according to the invention can be used in a method of treatment of an allergy and/or urticaria, said method comprising the administration of the pharmaceutical composition of the invention to a patient. The patient is preferably an infant or a child. By infant, it is meant a young human from birth to 1 year. By child, it is meant a young human from the age of 1 to 18 years.

A process for preparing a liquid pharmaceutical composition according to the invention is further disclosed, said process comprising the following steps:
- Mixing the pharmaceutically effective amount of fexofenadine and/or a pharmaceutically acceptable salt thereof with the pharmaceutically acceptable carrier which is either polyethylene glycol or a propylene glycol-based solvent, or a mixture thereof, to prepare a drug solution,
- Adding the pharmaceutical excipient stabilizing fexofenadine and/or a pharmaceutically acceptable salt thereof to the drug solution.

Finally, the use of glycerol, optionally in combination with sorbitol, for stabilizing fexofenadine and/or a pharmaceutically acceptable salt thereof in a liquid, is also disclosed by the present invention.

The invention is further defined by reference to the following illustrative examples that may be used to prepare or administer the compositions of the present invention. These examples are for illustrative purposes only, and not to be construed as limiting the appended claims.

EXAMPLE 1: LIQUID COMPOSITION COMPRISING FEXOFENADINE HYDROCHLORIDE STABILIZED BY GLYCEROL ONLY

1. Composition

A pharmaceutical composition according to the invention was prepared with the following ingredients:

| | | Composition A | | | | |
|---|---|---|---|---|---|---|
| S. No. | Ingredient Drug Solution | Grade or Trademark | mg/5 mL | g/5 mL | % w/w* | % w/v** |
| 1 | Fexofenadine | Fexofenadine hydrochloride (HCl) | 30 | 0.030 | 0.51 | 0.60 |
| 2 | Polyethylene Glycol | PEG 400 | 50 | 0.050 | 0.85 | 1.00 |
| 3 | Propylene Glycol | | 125 | 0.125 | 2.13 | 2.50 |
| S. No. | Flavoured Vehicle | | | | | |
| 4 | Glycerine | Speziol G 99.8% PF | 5000 | 5.000 | 85.2 | 100.00 |
| 5 | Flavouring agent | Raspberry | 15 | 0.015 | 0.26 | 0.30 |
| 6 | Xylitol | Xylosorb 90 | 300 | 0.300 | 5.11 | 6.00 |
| 7 | Sucralose | | 75 | 0.075 | 1.28 | 1.50 |
| 8 | Di-Sodium EDTA | | 7 | 0.007 | 0.12 | 0.14 |
| 9 | Purified Water | | Qs* (266.60) | 0.267 | 4.54 | 5.33 |
| | | | 5868.6 | 5.8686 | 100 | 117.372 |

The percentages of each ingredient are with respect to the total weight or volume of the composition.
*w/w: weight/weight.
**w/v: weight/volume
***Qs: quantum satis.

2. Preparation Process

| Step 1 | Dissolved/Stir polyethylene glycol (PEG 400) and propylene glycol in stirrer for 30 minutes. |
|---|---|
| Step 2 | Add fexofenadine hydrochloride and stir until a clear solution is obtained and continue stirring for 24 hours. |
| Step 3 | Add glycerin into step 2 and stir for 60 minutes. |
| Step 4 | Add raspberry/any suitable flavour into step 3 and stir for 60 minutes. |
| Step 5 | Dissolve di-sodium EDTA, sucralose, xylitol in purified water and transfer into step 4 and stir for 1 hour. |
| Step 6 | Transfer the final formulation into PET Bottle. |

The pH of the final liquid composition is 4.5±0.5. This composition comprises 30 mg of fexofenadine hydrochloride per 5 mL of syrup.

3. Stability Data:

The stability of the composition has been tested at 40° C. with a relative humidity of 75%, and at 25° C. with a relative humidity of 60%, by detecting and measuring the decomposition products of fexofenadine hydrochloride by using HPLC with UV detector.

The results are given in table 1 below:

TABLE 1

| Stability study result with composition A | | | | |
|---|---|---|---|---|
| | | 40° C./75% RH | | 25° C./ 60% RH |
| | Initial | 2 Months | 3 Months | 3 Months |
| Fexofenadine hydrochloride | 101.5 | 99.3 | 100.5 | 100.7 |
| Other detected substances | | | | |
| Impurity B | ND* | ND* | ND* | ND* |
| Impurity A | 0.021 | 0.032 | 0.026 | 0.019 |
| Impurity D | 0.008 | 0.005 | ND* | 0.007 |
| Impurity C | 0.005 | 0.005 | 0.006 | 0.007 |
| Single max. unknown | 0.005 | 0.120 | 0.112 | 0.095 |
| Total impurities | 0.063 | 0.281 | 0.278 | 0.218 |
| pH | 4.352 | 4.477 | 4.424 | 4.382 |

*ND: not detected

Impurity A: 2-[4-[4-[4-(hydroxydiphenylmethyl)piperidin-1-yl]butanoyl]phenyl]-2-methylpropanoic acid, Impurity B: 2-[3-[(1RS)-1-hydroxy-4-[4-(hydroxydiphenylmethyl)piperidin-1-yl]butyl]phenyl]-2-methylpropanoic acid, Impurity C: (1RS)-4-[4-(hydroxydiphenylmethyl)piperidin-1-yl]-1-[4-(1-methylethyl)phenyl]butan-1-ol, Impurity D: methyl 2-[4-[(1RS)-1-hydroxy-4-[4-(hydroxydiphenylmethyl)piperidin-1-yl]butyl]phenyl]-2-methylpropanoate EXAMPLE 2: ORAL LIQUID COMPOSITION COMPRISING FEXOFENADINE HYDROCHLORIDE STABILIZED BY A COMBINATION OF GLYCEROL AND SORBITOL 1. Composition A pharmaceutical composition according to the invention was prepared with the following ingredients

| | | Composition B | | | | |
|---|---|---|---|---|---|---|
| S. No. | Ingredient | Drug Solution | mg/5 mL | g/5 mL | % w/w* | % w/v |
| 1 | Fexofenadine | Fexofenadine hydrochloride | 30 | 0.030 | 0.49 | 0.60 |
| 2 | Polyethylene Glycol | PEG 400 | 50 | 0.050 | 0.81 | 1.00 |
| 3 | Propylene Glycol | | 125 | 0.125 | 2.03 | 2.50 |
| S. No. | Flavoured Vehicle | | | | | |
| 4 | Sorbitol Solution | Solution 70% w/w (Neosorb 70/70) | 2970 | 2.970 | 48.12 | 59.40 |
| 5 | Glycerine | Speziol G 99.8% PF | 2350 | 2.350 | 38.08 | 47.00 |
| 6 | Flavouring agent | Raspberry | 15 | 0.015 | 0.24 | 0.30 |
| 7 | Xylitol | Xylosorb 90 | 300 | 0.300 | 4.86 | 6.00 |
| 8 | Sucralose | | 75 | 0.075 | 1.22 | 1.50 |
| 9 | Di-Sodium EDTA | | 7 | 0.007 | 0.11 | 0.14 |
| 10 | Purified Water | | Qs* (250.00) | 0.250 | 4.05 | 5.00 |
| | | | 6172 | 6.172 | 100 | 123.44 |

The percentages of each ingredient are with respect to the total weight or volume of the composition.

*w/w: weight/weight.

**w/v: weight/volume

***Qs: quantum satis.

2. Preparation Process

| Step 1 | Stir polyethylene glycol and propylene glycol for 30 minutes. |
|---|---|
| Step 2 | Add fexofenadine hydrochloride into step1 and stir continuously until a clear solution is achieved. |
| Step 3 | Weigh sorbitol and glycerin then stir for 5 min and transfer to step 2 and stir for 1 hour. |
| Step 4 | Dissolve di-sodium EDTA, sucralose, xylitol in purified water and transfer into step 3 and stir for 30 minutes. |
| Step 5 | Add Raspberry/any suitable flavour into step 4 and stir for 30 minutes. |
| Step 6 | Transfer the final formulation into PET Bottle. |

The pH of the final liquid composition is 4.5±0.5. This composition comprises 30 mg of fexofenadine hydrochloride per 5 mL of syrup.

3. Stability Data:

The stability of the composition has been tested as mentioned in example 1.

The results are given in table 2 below:

TABLE 2

Stability study result with composition B

| | | 40° C./75% RH | | 25° C./ 60% RH 3 Months |
|---|---|---|---|---|
| | Initial | 2 Months | 3 Months | |
| Fexofenadine hydrochloride | 99.2 | 97.6 | 98.9 | 99.4 |
| Other detected substances | | | | |
| Impurity B | ND* | ND* | ND* | ND* |
| Impurity A | 0.014 | 0.026 | 0.031 | 0.028 |
| Impurity D | 0.023 | 0.020 | 0.021 | 0.023 |

TABLE 2-continued

Stability study result with composition B

| | | 40° C./75% RH | | 25° C./ 60% RH 3 Months |
|---|---|---|---|---|
| | Initial | 2 Months | 3 Months | |
| Impurity C | 0.008 | 0.010 | 0.009 | 0.009 |
| Single max. unknown | 0.019 | 0.017 | 0.022 | 0.025 |
| Total impurities | 0.095 | 0.097 | 0.127 | 0.136 |
| pH | 3.995 | 4.158 | 3.932 | 4.046 |

*ND: not detected

Impurity A: 2-[4-[4-[4-(hydroxydiphenylmethyl)piperidin-1-yl]butanoyl]phenyl]-2-methylpropanoic acid, Impurity B: 2-[3-[(1RS)-1-hydroxy-4-[4-(hydroxydiphenylmethyl)piperidin-1-yl]butyl]phenyl]-2-methylpropanoic acid, Impurity C: (1RS)-4-[4-(hydroxydiphenylmethyl)piperidin-1-yl]-1-[4-(1-methylethyl)phenyl]butan-1-ol, Impurity D: methyl 2-[4-[(1RS)-1-hydroxy-4-[4-(hydroxydiphenylmethyl)piperidin-1-yl]butyl]phenyl]-2-methylpropanoate

The invention claimed is:

1. A liquid pharmaceutical composition for oral administration comprising:
   a pharmaceutically effective amount of fexofenadine or a pharmaceutically acceptable salt thereof;
   0.05% wt. to 2% wt. of polyethylene glycol;
   1.3% wt. 3.5% wt. of propylene glycol;
   25% wt. to 50% wt. of glycerol;
   20% wt. to 50% wt. sorbitol; and
   less than 5% wt. of extra water, and wherein the composition is substantially free of glucose or sucrose;
   wherein the weight percentage is relative to the total weight of the composition.

2. The liquid pharmaceutical composition of claim 1, further comprising a sugar substitute, a chelating agent, a flavouring agent, or a combination of any of the foregoing.

3. A method of treating an allergy and/or urticaria in a patient in need thereof comprising administering the liquid pharmaceutical composition of claim 1 to the patient in need thereof.

4. A process for preparing the liquid pharmaceutical composition of claim 1, comprising the steps:
   mixing the fexofenadine or pharmaceutically acceptable salt thereof with the polyethylene glycol and the propylene glycol to prepare a drug solution;
   adding the glycerol and sorbitol to the drug solution; and
   adding the extra water to the resulting drug solution; and
   wherein the polyethylene glycol, propylene glycol, glycerol, sorbitol, and extra water are added within the weight percent ranges of claim 1.

5. The liquid pharmaceutical composition of claim 1, comprising 0.2% wt. to 1.5% wt. of polyethylene glycol.

6. The liquid pharmaceutical composition of claim 1, comprising 1.5% wt. to 2.5% wt. of propylene glycol.

7. The liquid pharmaceutical composition of claim 1, comprising 30% wt. to 45% wt. of glycerol.

8. The liquid pharmaceutical composition of claim 1, comprising 25% wt. to 40% wt. of sorbitol.

9. The liquid pharmaceutical composition of claim 1, having a pH of about 4.0 to about 5.0.

10. The liquid pharmaceutical composition of claim 1, comprising 0.05% wt. to 2% wt. of fexofenadine or a pharmaceutically acceptable salt thereof.

\* \* \* \* \*